(12) United States Patent
Coles et al.

(10) Patent No.: US 7,641,873 B2
(45) Date of Patent: Jan. 5, 2010

(54) TRANSESOPHAGEAL ULTRASONIC PROBE DISINFECTANT SYSTEMS

(75) Inventors: Philip Robert Coles, Haddam, CT (US); Gregory John Dobbyn, Creedmoor, NC (US)

(73) Assignee: Gregory J. Dobbyn

( * ) Notice: Subject to any disclaimer, the term of this patent is extended or adjusted under 35 U.S.C. 154(b) by 1062 days.

(21) Appl. No.: 10/519,017

(22) PCT Filed: Jun. 23, 2003

(86) PCT No.: PCT/US03/19784

§ 371 (c)(1),
(2), (4) Date: Dec. 21, 2004

(87) PCT Pub. No.: WO2004/011162

PCT Pub. Date: Feb. 5, 2004

(65) Prior Publication Data

US 2005/0215906 A1    Sep. 29, 2005

(51) Int. Cl.
*A61L 2/18* (2006.01)
*A61L 2/24* (2006.01)

(52) U.S. Cl. .................................. 422/300

(58) Field of Classification Search .............. None
See application file for complete search history.

(56) References Cited

U.S. PATENT DOCUMENTS

| 4,763,678 | A | * | 8/1988 | Ott ............................ 134/171 |
| 6,132,691 | A | * | 10/2000 | Coles ......................... 422/300 |
| 6,558,620 | B1 | * | 5/2003 | Sanford et al. ................ 422/28 |

* cited by examiner

*Primary Examiner*—Elizabeth L McKane
(74) *Attorney, Agent, or Firm*—Melvin I. Stoltz (57) ABSTRACT

By providing a single house (21) which incorporates an elongated probe (22) receiving zone interconnected to a pump member (55), a plurality of automated valves (51-54), a disinfectant dispensing chamber (20), a water supply (41), and a control system for automatically cycling each of the components to achieve the desired result, a fully automated disinfection system (20) for transesophageal ultrasonic probes is achieved. In accordance with the present invention, a simple, easily employed, convenient, fully integrated system (20) is attained for quickly and easily receiving the transesophageal ultrasonic probe in its entirety, supporting the electronic bearing head portion independently from the disinfection portion, and automatically performing various disinfection and rinse cycles for providing a completely disinfected ultrasonic probe member ready for use.

16 Claims, 8 Drawing Sheets

TRANSESOPHAGEAL ULTRASONIC PROBE DISINFECTANT SYSTEMS

TECHNICAL FIELD

This invention relates to transesophageal ultrasonic probe disinfectant systems and more particularly to fully automated computer-based disinfectant systems.

BACKGROUND ART

Due to the ever increasing use of electronics in the creation of medical equipment, new and improved systems have been developed for providing medical information using less invasive techniques. One of these developments which has become increasingly popular is the transesophageal ultrasonic probe.

Transesophageal ultrasonic probes are used to provide a graphic outline of the movement, valves, and chambers of a heart by employing high frequency sound waves generated from a small transducer mounted at the tip of an elongated, flexible member. In use, the transesophageal ultrasonic probe is passed down an individual's throat in order to place the transducer in the desired position for obtaining the information being sought. Once the desired information has been obtained, the probe is removed.

It has been found that ultrasonic probes provide non-invasive clear images of the heart's movement, since the transducer is near the heart without interfering with the heart. These images enable physicians to assess the function of the heart's chambers and valves, determine the presence of diseases of the heart muscles, valves, and pericardium, uncover tumors and congenital heart disease, and evaluate the effectiveness of treatments as well as evaluate heart abnormalities.

Although this system has become extremely popular, due to its efficacy in providing pertinent data in a reasonably non-invasive manner, care must be exercised in handling the probe and in disinfecting the probe for re-use. Since each probe is extremely costly, the probes are manufactured for repeated use and careful disinfection of the probe after each use must be performed.

Although transesophageal ultrasonic probes have become increasingly popular and widely used, no system presently exists which either automatically or even semi-automatically disinfects a transesophageal ultrasonic probe after use. Typically, most probes are disinfected manually and then undergo a manual high-level disinfection in a cold, liquid disinfectant. In this process, the disinfectant is allowed to remain in contact with the entire length of the probe member for an extended period of time in order to be certain that the entire outer surface has been fully treated and disinfected.

Since transesophageal ultrasonic probes comprise elongated, flexible members, which may have an overall length of about four feet with a transducer at one end and an electronic equipment bearing housing formed at the opposed end, manual handling of the probe provides numerous pitfalls and difficulties. In particular, the probe needs to be placed in a container or housing into which the disinfectant solution is placed for completely covering the probe. Then, the probe is allowed to remain in contact with the disinfectant solution for an extended period of time. In performing these steps, care must be exercised in being certain that the entire length of the probe is free from contact with any surface as well as any other portion of the probe.

Another problem typically encountered in the disinfection of ultrasonic probes is the difficulty encountered in handling the electronic bearing housing formed at one end of the probe. The probe's housing incorporates sensitive electronic connections and transmitter systems which interface with additional electronic equipment which receives data from the transducer, interprets the data, and produces the information output employed by the physicians in making their diagnosis. As a result, it is imperative that this housing is not exposed to the disinfectant, due to the potential harm and destruction that may occur. Consequently, the housing must be suspended or supported separate and apart from the remainder of the elongated ultrasonic probe, while all of the remainder of the probe is placed and retained in the liquid disinfectant.

A further major problem that occurs with disinfecting ultrasonic probes is the exposure each operator receives to the disinfectant's fumes. Due to the nature of the disinfectant employed, extremely limited exposure to individuals is recommended. However, due to the steps involved with the manual disinfection of ultrasonic probes, limiting an operator's exposure to the fumes becomes extremely difficult and problematic.

Therefore, it is a principal object of the present invention to provide a transesophageal ultrasonic probe disinfection system which is capable of providing a fully automated disinfection system which is completely computer controlled, requiring no handling by individuals.

Another object of the present invention is to provide an ultrasonic probe disinfection system having the characteristic features described above which completely eliminates any exposure of disinfectant fumes from the operator.

Another object of the present invention is to provide an ultrasonic probe disinfection system having the characteristic features described above which prevents any exposure of the disinfectant solution to the probe electronics.

Another object of the present invention is to provide an ultrasonic probe disinfection system having the characteristic features described above which enables a single use disinfectant holding container to be employed and disinfected after use.

Other and more specific objects will in part be obviated and will in part appear hereinafter.

SUMMARY OF THE INVENTION

By employing the present invention, all of the difficulties and drawbacks found in the prior art have been overcome, and a fully automated disinfection system for transesophageal ultrasonic probes is provided. In accordance with the present invention, a simple, easily employed, convenient, fully integrated system is achieved for quickly and easily receiving the transesophageal ultrasonic probe in its entirety, supporting the electronic bearing head portion independently from the disinfection portion, and automatically performing various disinfection, and rinse cycles for providing a completely disinfected ultrasonic probe member ready for use.

In accordance with the present invention, a single housing is provided which incorporates an elongated probe receiving zone which is interconnected to a pump member, a plurality of automated valves, a disinfectant dispensing chamber, a water supply, and a control system for automatically cycling each of the components to achieve the desired result. By employing this combination of elements and controlling the overall operation of each element in the precisely desired manner, a completely automated transesophageal ultrasonic probe disinfection system is realized.

In the preferred embodiment, the elongated probe receiving zone or cavity is constructed with an overall length greater than the length of the ultrasonic probe being disinfected. In addition, the probe receiving zone comprises a diameter greater than the probe diameter to assure ease of insertion and complete retention of the probe therein, while also preventing any contact between the probe and of the sidewalls of the receiving zone.

In the preferred construction, the disinfectant dispensing chamber is constructed for receiving a single use container which incorporates a highly concentrated disinfectant. Furthermore, the system automatically opens the container, and controllably dispenses the disinfectant from the container at the appropriate time directly onto the entire length of the probe.

In order to achieve the desired automated operation, the system of the present invention also incorporates a pump, a plurality of control valves, a water supply, and an electronic control system which is constructed for completely operating all of the required cycles and functions necessary to achieve the complete disinfection of the ultrasonic probe in a fully automated manner. In this way, all of the prior art failings are eliminated and a fully automated system is realized.

The present invention also incorporates a housing support and holding platform formed directly adjacent the elongated probe receiving cavity/zone whereby the sensitive electronic components contained in the housing are carefully supported, free from potential damage. The housing support and holding platform is also positioned to enable the entire length of the ultrasonic probe to be exposed to the disinfecting solutions for attaining the desired results.

Finally, all of the components are contained in a single housing which incorporates a cover member for preventing leakage of the fumes from the disinfectant solution into the surrounding ambient air. Furthermore, in order to further enhance the air quality and prevent any unwanted exposure or leakage of fumes into the ambient air, an air filtration system is also incorporated into the housing to remove any excess fumes generated by the disinfectant during its dispensing and use.

The invention accordingly comprises the features of construction, combination of elements and arrangement of parts which will be exemplified in the construction hereinafter set forth, and the scope of the invention will be indicated in the claims.

THE DRAWINGS

For a fuller understanding of the nature and objects of the invention, reference should be had to the following detailed description taken in connection with the accompanying drawings, in which.

DETAILED DISCLOSURE

By referring to FIGS. 1-10, along with the following detailed discussion, the construction and operation of the two alternate embodiments of the automated, transesophageal ultrasonic probe disinfection system of the present invention can best be understood. It is to be understood, however, that the embodiments detailed herein are provided for exemplary purposes only, since further alternate constructions and variations may be employed without departing from the present invention. Consequently, all variations and alternate constructions are intended to be within the scope of the present invention.

In FIGS. 1-4, a preferred embodiment of transesophageal ultrasonic probe disinfection system 20 of the present invention is depicted incorporating housing 21, which contains all of the components for providing an effective, automated, computer controlled disinfection system 20. As is evident from these depictions, this embodiment of ultrasonic probe disinfection system 20 comprises a free-standing unit, which is easily placed in any desired location.

Figure 1:
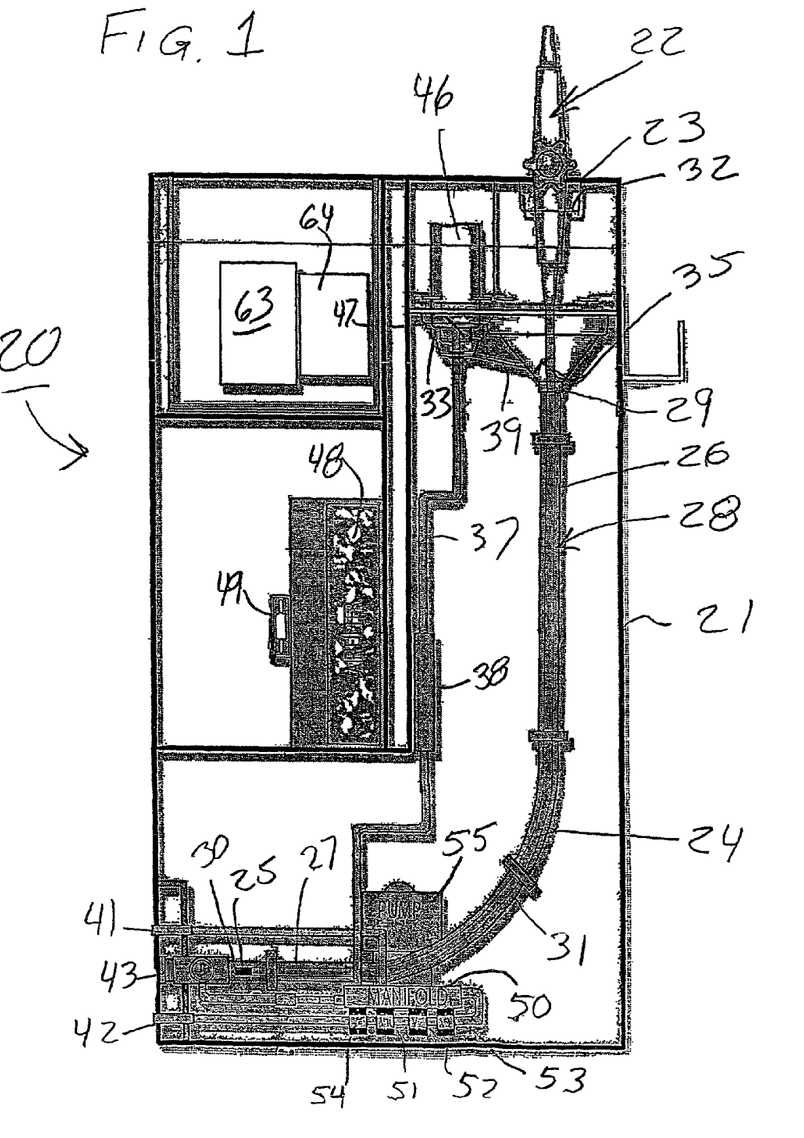
FIG. 1 is a front elevation view of the fully assembled, automated disinfection system of the present invention with the cover of the housing removed and with a transesophageal ultrasonic probe assembly mounted therewith.

As best seen in FIG. 1, housing 21 is shown with transesophageal ultrasonic probe assembly 22 supportingly retained therewith. As depicted, transesophageal ultrasonic probe assembly 22 comprises electronics containing section 23 forming one end of probe assembly 21, with section 23 directly connected to elongated flexible shaft 24. Elongated, flexible shaft 24 terminates at its opposed end with transducer 25.

In the preferred construction of this embodiment of the present invention, housing 21 of automated disinfection system 20 comprises an elongated, probe receiving and holding cavity or passageway 28 which is formed in housing 21, extending therein with an overall length greater than the length of flexible shaft 24 and transducer 25. In the preferred construction, as depicted in FIG. 1, probe receiving and holding cavity/passageway 28 comprises an elongated, continuous, pathway constructed for enabling shaft 24 with transducer 25 to be easily advanced into secure retained engagement therein. Furthermore, in order to enhance the ease of sliding engagement of shaft 24 and transducer 25 therein, cavity/passageway 28 is preferably formed from low-friction material, such as high density polyethylene or Teflon.

In the preferred construction, elongated probe receiving cavity/passage-way 28 comprises an elongated, longitudinally extending fully enclosed pathway, extending from entry portal 29 to terminating end 30. In this preferred embodiment, passageway 28 comprises two separate, substantially straight sections 26 and 27, in combination with one, intermediately positioned curved section 31. As further discussed below, passageway 28 may comprise a wide variety of shapes in order to accommodate the entire length of flexible shaft 24. In general, the particular shape or configuration employed is controlled by the overall size desired for housing 21, while providing ease of use and insertion of probe assembly 22 therein.

In addition, the diameter of cavity/passageway 28 is constructed to be greater than the diameter of elongated shaft 24, thereby enabling transducer 25 and shaft 24 to be easily inserted into portal 29 and telescopically advanced into cavity/passageway 28 along substantially the entire length thereof, until flexible shaft 24 and transducer 25 are completely retained within cavity/passageway 28. Although the diameter of cavity/passageway 28 may comprise any desired dimension, the preferred diameter ranges between about 0.5 inches and 2.0 inches.

In order to further enhance the ability of automated system 20 to provide the desired thorough disinfection of flexible shaft 24 and transducer 25, in the manner detailed below, this embodiment of elongated cavity/passageway 28 is formed in housing 21 in a vertically oriented, downwardly extending and sloping configuration, starting with portal 29 and terminating at end 30. In the preferred construction, straight section 27 is pitched downwardly, enabling terminating end 30 to be the lowermost portion of passageway 28.

By employing this construction, gravity forces cause any rinsing fluid or disinfecting solution to automatically cascade along the entire length of cavity/passageway 28, while simultaneously contacting the entire outer surface of shaft 24 and transducer 25. As a result, the desired disinfection of shaft 24 and transducer 25 are attained and enhanced.

As discussed above, and clearly shown in FIGS. 1 and 3-4, housing 21 incorporates holding and supporting platform 32 mounted to the top surface of housing 21, directly adjacent portal 29 and cavity/passageway 28. As depicted, holding and supporting platform 32 is constructed for securely retaining and supportingly holding electronics containing section 23 of ultrasonic probe assembly 22 in a manner which protects the electronics contained therein and prevents any exposure of the electronics contained in section 23 to the disinfection solutions and/or rinse water. In this way, assurance is provided that the entire length of flexible shaft 24 and transducer 25 are completely disinfected, while the electronics contained in section 23 is maintained free from exposure to any liquid.

Another feature of the present invention is the incorporation of docking station 33 integrally mounted to housing 21 and constructed for receiving and automatically opening specially constructed disinfectant solution container 46. In the present invention, a special, high concentration level of glutaraldehyde is preferred as the disinfecting solution. However, other commercially acceptable disinfection solutions can be employed with equal efficacy. One such alternate disinfectant solution is ortho-phthalaldehyde.

Although concentration may vary, depending upon particular desired results, it has been found that the glutaraldehyde concentration preferably ranged between about 2.25% and 3.0% by weight based upon the weight of the entire composition, with a concentration of 2.65% by weight being preferred. If ortho-phthalaldehyde is employed, the concentration preferably ranges between about 0.25% and 0.75% by weight based upon the weight of the active composition, with a concentration of 0.55% by weight being preferred.

In order to prevent unwanted handling of the disinfecting solution as well as prevent unwanted exposure to the fumes produced by glutaraldehyde, the concentrated glutaraldehyde employed in the present invention is preferably distributed in sealed containers 46, with each container 46 having the precise quantity of glutaraldehyde required for a single disinfecting cycle. In this way, prepackaged, sealed container 46 of concentrated glutaraldehyde is inserted into docking station 33, when desired, and activated for use when probe assembly 22 is securely mounted to housing 21, ready for disinfection.

In the present invention, docking station 33 is constructed incorporating upstanding, seal piercing member 47 which automatically punctures and breaks the seal formed on the glutaraldehyde container 46, enabling the delivery of the glutaraldehyde directly to probe receiving and holding cavity/passageway 28. In the preferred construction, piercing element 47 of docking station 33 pierces the seal formed on disinfectant bearing container 46 by incorporating elongated prongs which rupture the seal of container 46 and enter the interior of container 46. In addition, the prongs are connected with tubing, pumps, and valves, as detailed below, to draw the disinfectant solution from container 46 and deliver the disinfectant solution to cavity/passageway 28.

In the preferred construction of this embodiment of the present invention, housing 21 incorporates a disinfectant retaining reservoir 35 in the form of basin 36, which receives the disinfecting solution from dispensing container 46 and holds a quantity of the solution therein, if needed, as the solution enters portal 29 of cavity/passageway 28.

In this embodiment, when glutaraldehyde is employed, the disinfecting solution is heated prior to initiating the probe disinfection cycle and, once the desired temperature is attained, the solution is continuously circulated through passageway 28 in order to assure that the entire flexible shaft 24 of ultrasonic probe assembly 22 is completed disinfected.

In order to provide the desired circulation of the disinfecting solution during the disinfection cycle, ultrasonic probe disinfection system 20 incorporates elongated conduit 37 and heater 38 which is integrally associated with conduit 37. As is fully detailed below, this embodiment of the present invention incorporates manifold 50 which is interconnected to the distal end of passageway 28, while also being cooperatively associated with a plurality of circulation control valves. As shown and discussed below, the valves include valve (V1) 51, valve (V2) 52, valve (V3) 53, and valve (V4) 54. In addition, system 20 also comprises pump 55 for producing the desired circulation. Furthermore, one end of elongated conduit 37 is connected to manifold 50, while the opposed end of conduit 37 is connected to docking station 33 and seal piercing element 47.

System 50 also incorporates interconnecting tube member 39 which is mounted in direct association with docking station 33 and basin 36. In the preferred construction, tube member 39 extends between one end of conduit 37 and the proximal end of passageway 28. By employing this construction, a completely closed loop, fluid flow system is attained for enabling the disinfection solution to completely fill passageway 28 while also being continuously circulated therethrough during the disinfecting or heat/soak cycle. In addition to assuring that all of the disinfectant solution is effectively and efficiently circulated through cavity/passageway 28, this construction also disinfects the portion of flexible shaft 24 which is affixed directly to section 23, preventing any unwanted cross-contamination.

If ortho-phthalaldehyde is employed as the disinfectant solution, the heating of the solution described above can be avoided. However, due to the viscous, oily nature of ortho-phthalaldehyde, numerous rinsing cycles must be employed to remove all of the disinfectant from flexible shaft 24. Furthermore, if desired, heater 38 may be employed to heat the rinse water in order to obtain a more thorough and complete removal of all disinfectant. In addition, if desired, the use of fan 49 and filter 48 may be eliminated, since ortho-phthalaldehyde does not possess a strong odor.

Figure 2:
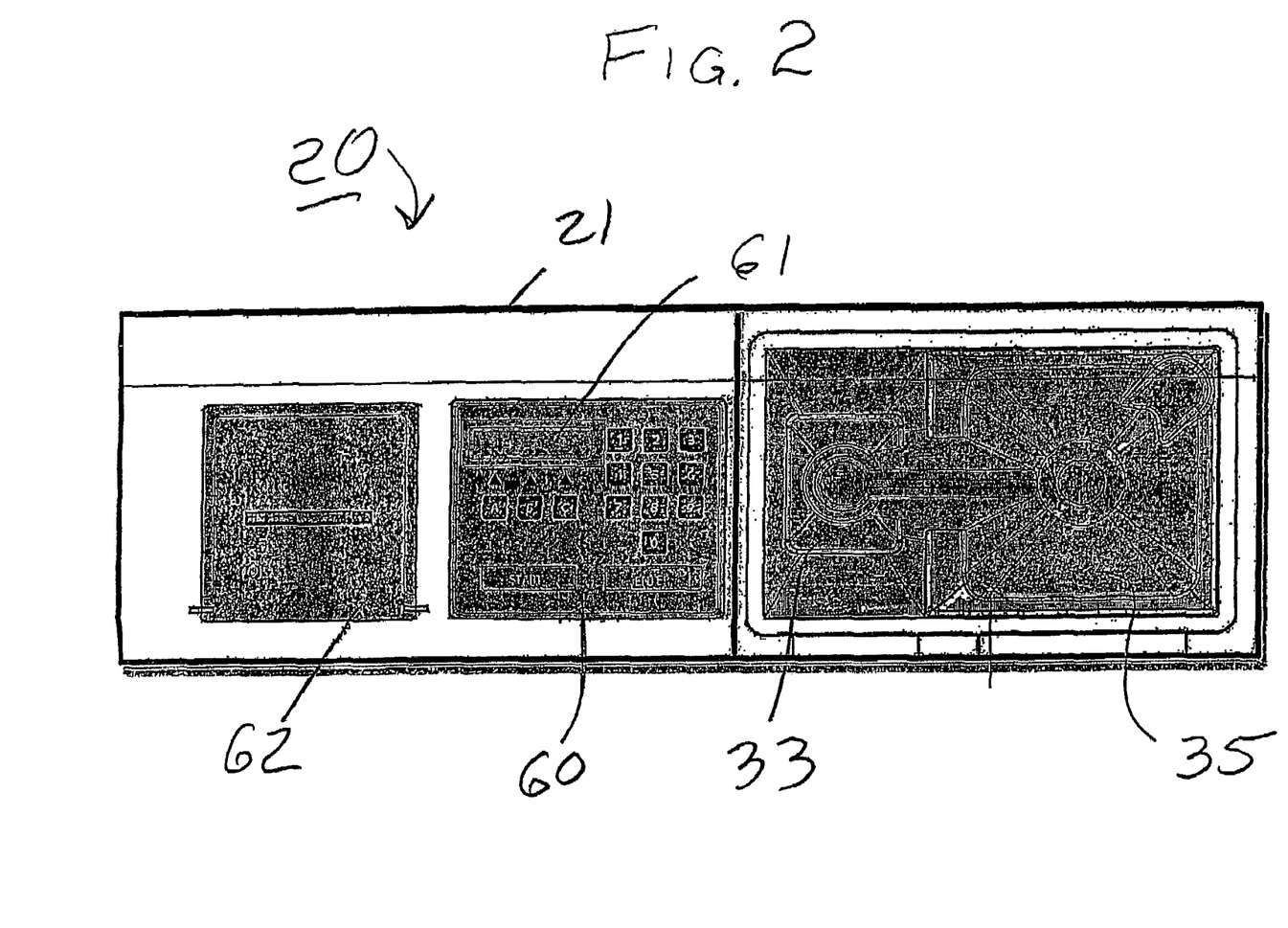
FIG. 2 is a top plan view of the fully assembled, automated disinfection system of FIG. 1.
Figure 3:
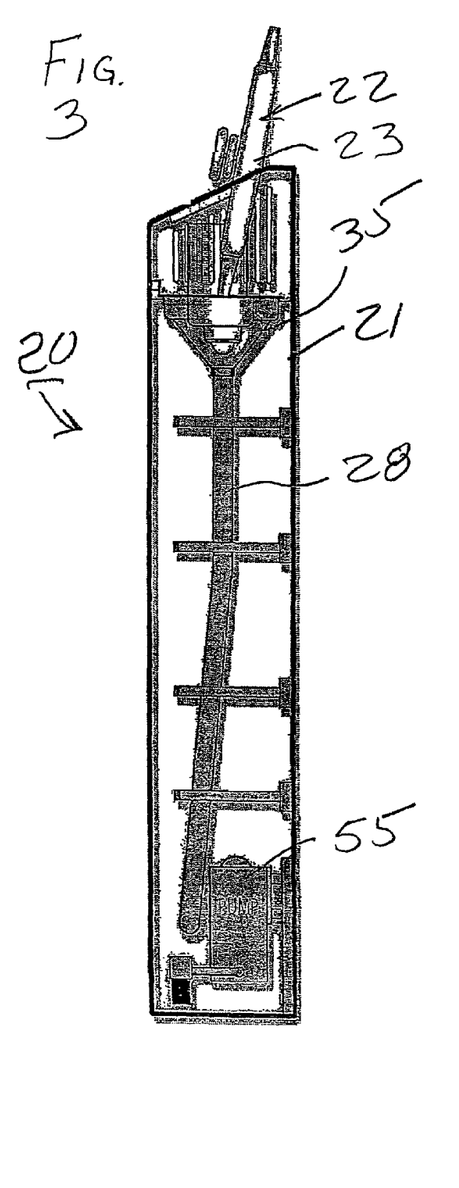
FIG. 3 is a side elevation view of the fully assembled, automated disinfection system of FIG. 1 looking from the right side of FIG. 1.
Figure 4:
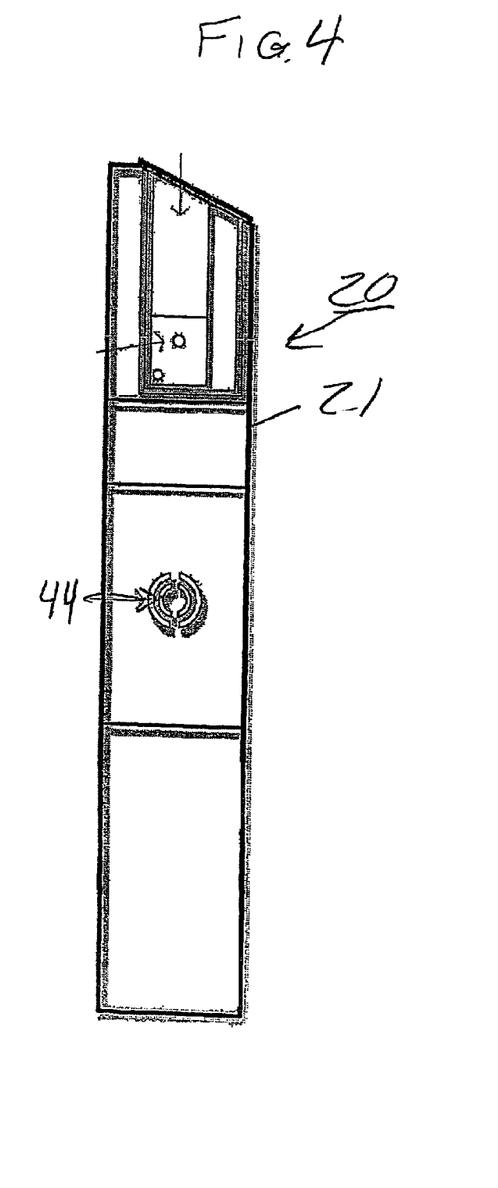
FIG. 4 is a side elevation view of the fully assembled automated disinfection system of FIG. 1, looking from the left side of FIG. 1.

As mentioned above, transesophageal fully assembled, automated disinfection system 20 of the present invention incorporates pump 55 and valves 51, 52, 53, and 54 which are controlled by a computer based electronic control system which produces the desired disinfection cycles for fully and completely disinfecting the entire length of flexible shaft 24 and transducer 25 of ultrasonic probe 22. All of these components are contained within housing 21 and are activated and controlled by keypad 60 of panel 40 which is mounted on the top surface of housing 21, as shown in FIG. 2. In addition, display screen 61 is also mounted on panel 40 for providing information to the user, along with printer assembly 61 which is also associated with panel 40. Finally, printed circuit boards 63 and 64 are mounted in housing 20 in association with panel 40 for providing the desired operational control.

In the preferred construction, the computerized control electronics provided by printed circuit board 63 and 64 operates the pumps and valves contained in housing 21 in a precisely desired cyclical sequence as defined by the built-in software forming a part thereof. By referring to FIG. 6, the fully integrated, computer based electronic control network employed in the present invention can be seen and understood. The predetermined sequence is more fully discussed below and provides a plurality of rinse cycles and disinfecting cycles which provide all of the required operations to attain a completely disinfected probe assembly in a fully automated manner. In the preferred construction, the system status is continuously displayed on display screen 61 of panel 40, with keypad 60 incorporating control buttons for initiating, overriding, or altering of the automated system, as required.

In the preferred construction, ultrasonic probe disinfection system 20 of the present invention also incorporates connections or fittings mounted to housing 21 for providing water inlet 41, waste outlet 42, and passageway cleanout 43. In the preferred construction, water inlet 41 incorporates water filtration components mounted therein, constructed for assuring that any water delivered to housing 21 is filtered to a high level or standard for use by system 20 in providing the desired disinfection of probe assembly 22.

Finally, housing 21 of system 20 of the present invention also preferably comprises a completely self-contained, fully enclosed unit for controlling the fumes produced by the system's operation when fume producing disinfectants are employed. In this regard, cover means are employed for overlying and covering all areas where fumes from the disinfecting solution could escape, such as docketing station 33, reservoir 36 and the holding zone for electronic section 23. In this way, exposure of the fumes of the disinfecting solution to individuals is prevented.

Furthermore, in the preferred construction, an air filtration system is incorporated into housing 21 which preferably incorporates air filters 48 constructed to remove and neutralize the disinfectant fumes generated by the solution. In its preferred construction, a blower or fan 49 is also employed to control the air flow in housing 21, and deliver the air through the filter before recirculating the filtered air into the ambient surroundings through outlet 44 shown in FIG. 4.

By employing ultrasonic probe disinfection system 20 of the present invention, any desired transesophageal ultrasonic probe can be quickly and easily mounted in system 20 of the present invention and completely disinfected in a fully automated, computer-controlled, easily employed manner. Typically, the first step employed by any operator in assuring that the desired trans-esophageal ultrasonic probe is properly disinfected is to remove any bio-burden on the probe assembly by employing an enzyme coated wipe sponge. By thoroughly disinfecting all bio-burden from the probe assembly, by merely drawing the elongated shaft and transducer through the enzyme coated wipe sponge, all human protein on the surface of the shaft is removed. This manual wiping process also mechanically removes the bio-burden that may remain on the probe from a previous patient.

Once the outer surface of the flexible shaft of the probe assembly has been manually wiped, the probe assembly is loaded into ultrasonic probe disinfection system 20 of this invention. As fully detailed above, this loading is quickly and easily achieved by telescopically advancing transducer 25 and flexible shaft 25 into elongated, probe receiving and holding cavity/passageway 28. Once the entire length of flexible shaft 24 of probe assembly 22 has been fully extended into cavity/passageway 28, electronics containing section 23 is mounted to holding and supporting platform 32, where section 23 is securely retained with the electronics thereof secured and positioned for preventing any exposure thereof to any disinfecting solutions and/or rinse water.

If desired, display screen 61 of panel 40 may initially display a request for the operator to select whether a leak test should be performed on probe assembly 22. If the leak test is desired, a salt tablet is placed in cavity/passageway 28 prior to loading probe assembly 22 therein and, once the probe assembly has been fully inserted into cavity/passageway 28, the start button on keypad 60 of panel 40 is pressed to begin the process.

Figure 5:
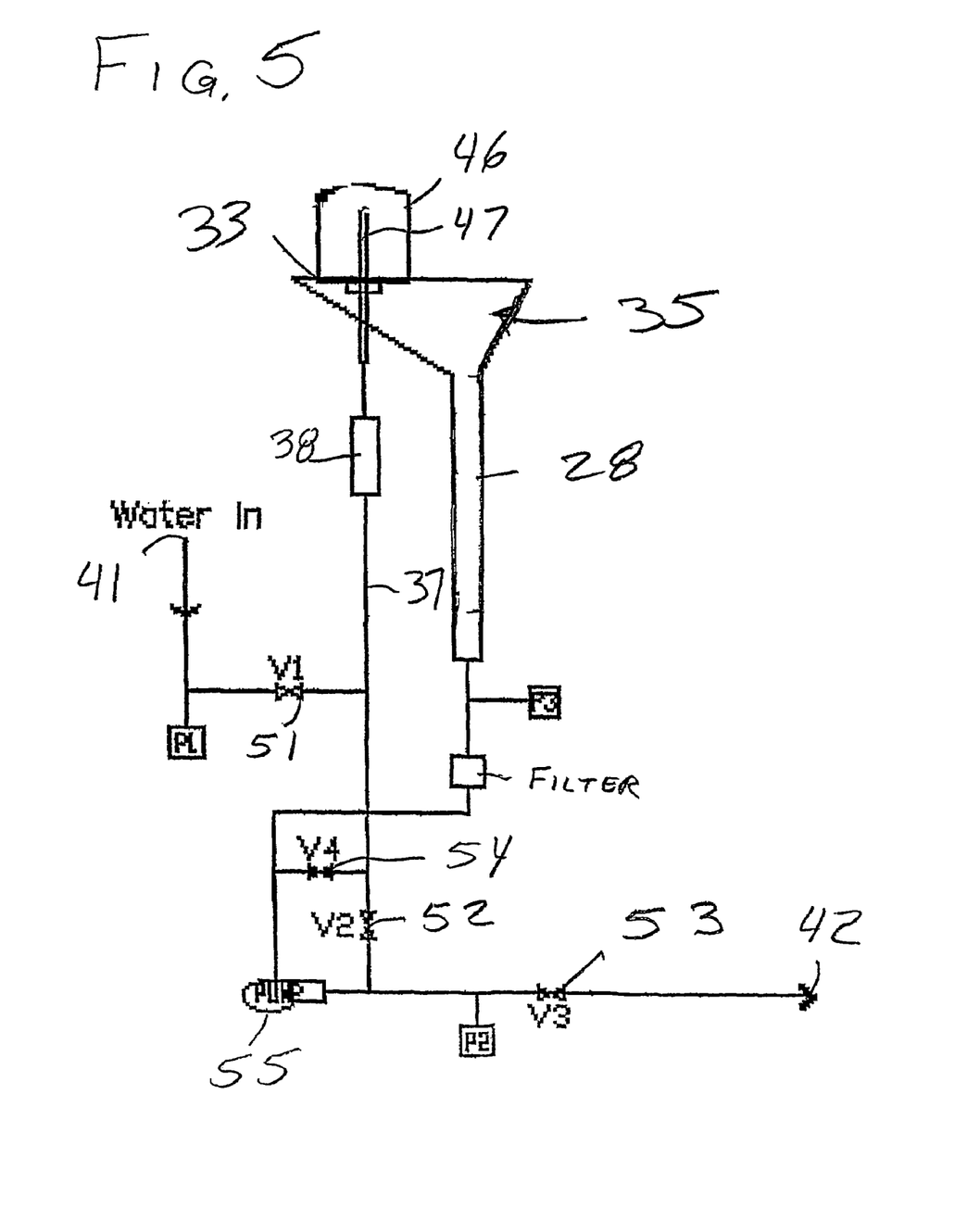
FIG. 5 is a schematic diagrammatic view of the automated disinfection system of the present invention showing the layout of the component incorporated into the disinfection system of the present invention.

By referring to FIG. 5, along with the following detailed discussion, the automated operation of ultrasonic probe disinfection system 20 of the present invention can best be understood. In addition, the automated opening and closing of the cooperating valve members associated with system 20 are discussed in conjunction with the depiction of these valve members in FIG. 5.

Once the probe assembly is mounted in place, the next step in the process is to mount sealed disinfectant bearing container 46 in docking station 33 which automatically causes the seal to be ruptured to enable the disinfectant solution to be withdrawn from container 46. At this time, housing 20 should be enclosed by the associated cover to assure that fumes generated by the disinfectant solution are controlled and the operator is not exposed to the fumes.

At this stage, disinfecting system 20 automatically cycles through each of the pre-determined stages which assures that probe assembly 22 is fully disinfected. In the preferred construction of this embodiment, the first cycle is a disinfectant fill cycle, wherein the entire contents of container 46 is allowed to fill passageway 28, peripherally surrounding flexible shaft 24 of probe 22. In order to achieve this cycle, all of the valves remain closed, with heater 38 and pump 55 set to "OFF".

In the next cycle, the disinfectant is heated and shaft 24 of probe 22 is soaked with the heated disinfectant. In order to achieve the desired thorough soaking and disinfection of shaft 24 of probe 22, heater 38 is turned on, pump 55 is activated, and valve (V2) 52 is opened. In this way, the heated disinfectant is continuously circulated through passageway 28, conduit 37, heater 38, and reservoir 35 through tube member 39 (shown in FIG. 1).

In order to achieve the desired level of disinfection of shaft 24, the disinfectant solution is heated to a temperature ranging between about 35° C. and 45° C. At this temperature level, a circulation time ranging between about 4 minutes and 10 minutes provides the desired disinfection of shaft 24.

In order to assure that the temperature of the disinfection solution is maintained at the desired level throughout the heat/soak cycle, temperature sensors are mounted in various locations of system 20 for continuously measuring the temperature of the circulating, disinfectant solution. Although numerous temperature sensors may be placed in numerous alternate positions, four sensors are preferably positioned in the following preferred locations: (1) reservoir 35 at entry portal 29 of passageway 28, (2) terminating end 30 of passageway 28, (3) on heater 38, and (4) in heater 38.

Once the heat/soak cycle is completed, the disinfectant purge cycle is initiated. In this cycle, the disinfectant is drained from the system to waste drain 42. In order to achieve this result, heater 38 is turned off, pump 55 continues to operate, and valves 53 and 54 are opened, with valve 52 remaining open. In this way, all of the disinfectant solution contained in passageway 28, conduit 37, reservoir 35 and tube member 39 is completely removed and drained from system 20. Generally, it has been found that this cycle should continue for about two minutes, in order to assure complete removal of the disinfectant solution.

In the next step, the disinfectant bearing container and delivery lines are automatically cleaned and flushed. In achieving this result, valve 51 is opened whiles valve 52, 53, and 54 are closed for a period of time just long enough to fill the disinfectant bearing container 46, passageway 29 and reservoir 35 with water from water inlet 41. Once filled with water, valve (V1) 51 is closed, valve (V2) 52 is opened, and pump 55 is turned on. Then, with valves (V3) 53 and (V4) 54 closed, water is circulated through system 20 in order to thoroughly rinse all lines and shaft 24 to remove any residual disinfectant.

Once the water has circulated for an appropriate period of time, such as 30 seconds to 3 minutes, the rinse water is purged from system 20. With pump 55 on, and valve 51 closed, valves 53 and 54 are opened, with valve 52 remaining open In this way, all of the rinse water in system 20 is withdrawn and delivered to waste outlet 42.

In the final steps, a final rinse and purge of cavity/passageway 28, conduit 37 and reservoir 35 is provided. Preferably, the final rinse is conducted for approximately two to four minutes in order to remove all traces of the disinfectant therefrom. In the final purge/rinse cycle, pump 5 is on, valves 51 and 53 are opened, and valves 52 and 54 are closed. In this way, water is allowed to circulate throughout system 20.

Once the final rinse cycle has been concluded, the final purge is achieved by closing valve 51, opening valves 52, 53, and 54, with water pumps 55 on. In this way, all of the water in cavity/passageway 28, conduit 37, and reservoir 35 is delivered to drain 42.

Although fully detailed above, Table I is provided for assuring a full and complete disclosure of the pump and valve sequencing. As is evident from a review of Table I, the pump and valve control operation and status for each of the steps is provided.

If desired, pressure sensors may be employed in order to be certain that a sufficient quantity of disinfectant is in passageway 28, as well as checking the water pressure at various locations. In FIG. 5, the use of placement of three pressure sensors are shown and depicted as P1, P2, and P3.

TABLE I

MACHINE CYCLES

| MACHINE CYCLE | HARDWARE CONDITION (ON/OFF) | | | | | |
|---|---|---|---|---|---|---|
| | HEATER | PUMP | VALVE 1 | VALVE 2 | VALVE 3 | VALVE 4 |
| System Initialized | OFF | OFF | CLOSED | CLOSED | CLOSED | CLOSED |
| Disinfectant Fill | OFF | OFF | CLOSED | CLOSED | CLOSED | CLOSED |
| Heat/Soak | ON | ON | CLOSED | OPEN | CLOSED | CLOSED |
| Disinfectant Purge | OFF | ON | CLOSED | OPEN | OPEN | OPEN |
| Fill/Rinse | OFF | OFF | OPEN | CLOSED | CLOSED | CLOSED |
| Rinse/Circulate | OFF | ON | CLOSED | OPEN | CLOSED | CLOSED |
| System Purse | OFF | ON | CLOSED | OPEN | OPEN | OPEN |
| Purge/Rinse | OFF | ON | OPEN | CLOSED | OPEN | CLOSED |
| Final Purge | OFF | ON | CLOSED | OPEN | OPEN | OPEN |

Once all of the cycles have been completed, panel 40 displays an appropriate message, such as cycle end, and ultrasonic probe assembly 22 is completely disinfected, ready to be removed and re-used. Furthermore, in the preferred embodiment, a printer assembly 62 is interconnected with system 20 and provides a complete summary of the machine operation and a validation of the procedure and its completion.

Figure 6:
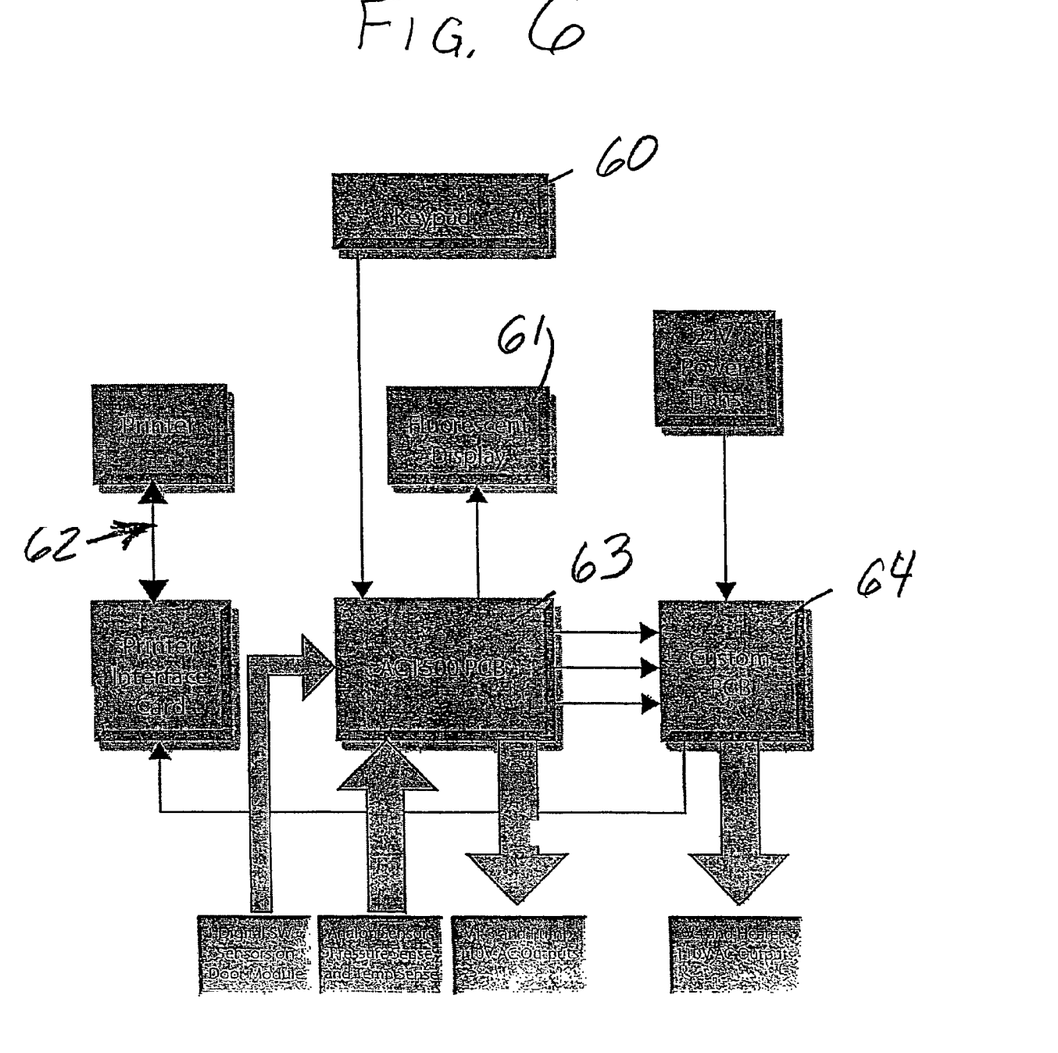
FIG. 6 is a schematic diagrammatic view of the computer controlled electronic network employed in the present invention.
Figure 7:
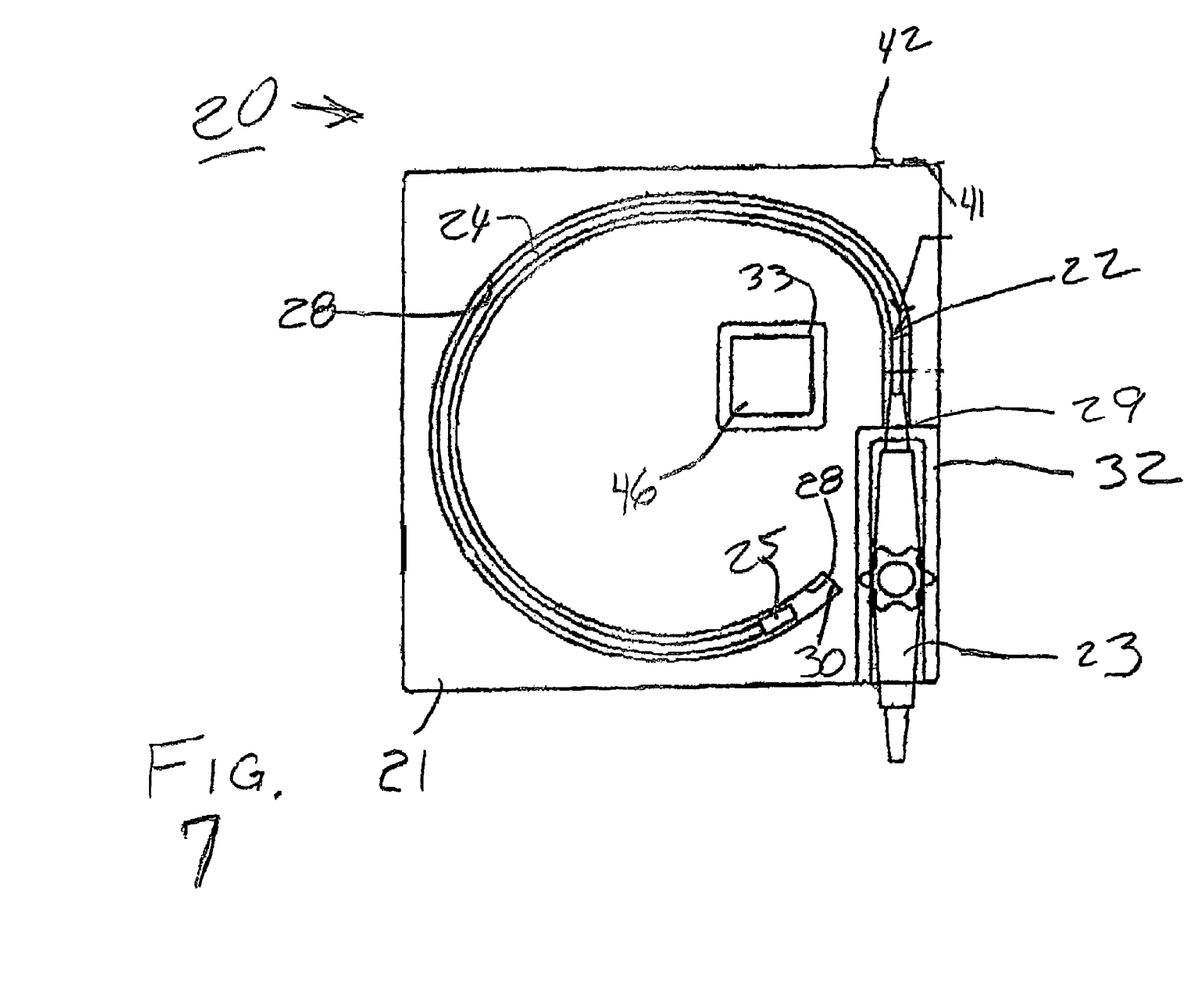
FIG. 7 is a top plan view of the fully assembled, automated disinfection system of the present invention.
Figure 8:
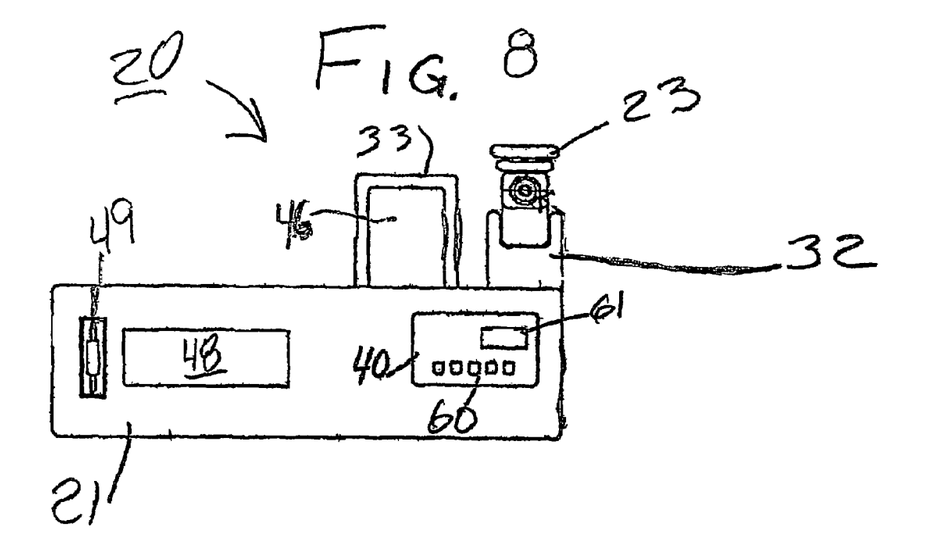
FIG. 8 is a front elevation view of the fully assembled, automated disinfection system of FIG. 1.

In FIGS. 6-8, an alternate embodiment of transesophageal ultrasonic probe disinfecting system 20 of the present invention is depicted incorporating housing or base 21, which contains all of the components for providing an effective, automated disinfecting system 20. As best seen in FIG. 6, housing 21 is shown with transesophageal ultrasonic probe assembly 22 supportingly retained therewith. As depicted, transesophageal ultrasonic probe assembly 22 comprises electronics containing section 23 forming one end of probe assembly 21, with section 23 directly connected to elongated flexible shaft 24. Elongated, flexible shaft 24 terminates at its opposed end with transducer 25.

In the preferred construction of this embodiment of the present invention, housing 21 of automated disinfecting system 20 comprises an elongated, probe receiving and holding cavity or passageway 28 which is formed in housing 21, extending therein with an overall length greater than the length of flexible shaft 24 and transducer 25. In the preferred construction, as depicted in FIG. 6, probe receiving and holding cavity/passageway 28 comprises an elongated, continuous, arcuately curved pathway constructed for enabling shaft 24 with transducer 25 to be easily advanced into secure retained engagement therein. Furthermore, in order to enhance the ease of sliding engagement of shaft 24 and transducer 25 therein, cavity/passageway 28 is preferably formed from low-friction material, such as high density polyethylene or Teflon.

In the preferred construction, elongated probe receiving cavity/passage-way 28 comprises an arcuately curved, helically shaped, fully enclosed pathway, extending from entry portal 29 to terminating end 30. In addition, the diameter of cavity/passageway 28 is constructed to be greater than the diameter of elongated shaft 24, thereby enabling transducer 25 and shaft 24 to be easily inserted into portal 29 and telescopically advanced into cavity/passageway 28 along substantially the entire length thereof, until flexible shaft 24 and transducer 25 are completely retained within cavity/passageway 28. Although the diameter of cavity/passageway 28 may comprise any desired dimension, the preferred diameter ranges between about 0.5 inches and 2.0 inches.

In order to further enhance the ability of automated system 20 to thoroughly provide the desired thorough disinfection of flexible shaft 24 and transducer 25, in the manner detailed below, elongated cavity/passageway 28 is formed in housing 21 with a gentle, downwardly sloping configuration, starting with portal 29 and terminating at end 30. In the preferred construction, terminating end 30 is formed at least 1.5 inches to 2.0 inches lower than portal 29.

In this way, gravity forces cause any rinsing fluid or disinfecting solution to automatically cascade along the entire length of cavity/passageway 28, while simultaneously contacting the entire outer surface of shaft 24 and transducer 25. As a result, the disinfection of shaft 24 and transducer 25 are enhanced.

As discussed above, and clearly shown in FIGS. 6-8, housing 21 incorporates holding and supporting platform 32 mounted to the top surface of housing 21, directly adjacent portal 29 and cavity/zone 28. As depicted, holding and supporting platform 32 is constructed for securely retaining and supportingly holding electronics containing section 23 of ultra-ultrasonic probe assembly 22 in a manner which protects the electronics contained therein and prevents any exposure of the electronics contained in section 23 to the disinfecting solutions and/or rinse water. In this way, assurance is provided that the entire length of flexible shaft 24 and transducer 25 are completely disinfected, while the electronics contained in section 23 is maintained free from exposure to any liquid.

Another feature of the present invention is the incorporation of docking station 33 integrally mounted to housing 21 and constructed for receiving and automatically opening a specially constructed disinfectant solution container. In the present invention, a special, high concentration level of glutaraldehyde is employed as the disinfecting solution. In order to prevent unwanted handling of the disinfecting solution as well as prevent unwanted exposure to the fumes produced by glutaraldehyde, the concentrated glutaraldehyde employed in the present invention is preferably distributed in sealed containers, with each container having the precise quantity of glutaraldehyde required for a single cleaning cycle. In this way, the prepackaged, sealed container of concentrated glutaraldehyde is inserted into docking station 33, when desired, and activated-for use when probe assembly 22 is securely mounted to housing 21, ready for being disinfected.

In the present invention, docking station 33 is constructed for automatically breaking the seal formed on the glutaraldehyde container and for delivering the glutaraldehyde directly to portal 29 of probe receiving and holding cavity/passageway 28. In the preferred embodiment, as best seen in FIG. 8, housing 21 incorporates a disinfectant retaining reservoir 35 which receives the disinfecting solution from the dispensing container and holds a quantity of the solution therein as the solution enters portal 29 of cavity/passageway 28.

In the preferred construction, docking station 33 pierces the seal formed on the disinfectant bearing container and incorporates prongs which engage in the container and is connected with tubing, pumps, and valves, as detailed below, to draw the disinfectant solution from the container and deliver the disinfectant solution to cavity/zone 28.

In addition, sidewall 70 of reservoir 35 incorporates a solution delivery inlet 71 which is connected to cavity/passageway 28 through control valves and pumps for delivering quantities of the disinfecting solution to cavity/passageway 28. In this way, assurance is provided that all of the disinfecting solution is delivered to cavity/passageway 28 for exposing flexible shaft 24 in its entirety to the disinfecting solution.

Furthermore, housing 21 preferably incorporates overflow control tube or weir 72 to be certain that the disinfecting solution does not overflow from cavity/passageway 28 during the filling process. By employing the overflow control tube or weir 72, assurance is provided that all of the disinfecting solution is delivered directly to cavity/passageway 28 for use in disinfecting the entire length of flexible shaft 24, and any backflow created from delivering the disinfectant solution to cavity/passageway 28 too quickly is accommodated by having any such backflow returned to reservoir 35 for delivery to cavity/passageway 28. In addition to assuring that all of the disinfectant solution is effectively and efficiently transferred to cavity/passageway 28, this construction also disinfects the portion of flexible shaft 24 which is affixed directly to section 23, preventing any unwanted cross-contamination.

As is more fully detailed below, transesophageal ultrasonic probe disinfecting system 20 of the present invention incorporates a pump and a plurality of valves which are controlled by an electronic control system which produces the desired disinfecting cycles for fully and completely disinfecting the entire length of flexible shaft 24 and transducer 25 of ultrasonic probe 22. All of these components are contained within housing 21 and are activated and controlled by panel 40 mounted on the front wall of housing 21.

In the preferred construction of this embodiment, the control electronics operates the pumps and valves contained in housing 21 in a precisely desired cyclical sequence as defined by the built-in software forming a part thereof. The predetermined sequence is more fully discussed below and provides a plurality of rinse cycles and disinfecting cycles which provide all of the required operations to attain a completely disinfected probe assembly in a fully automated manner. In the preferred construction, the system status is continuously displayed on panel 40 which also incorporates control buttons for overriding or altering of the automated system, if required.

In the preferred construction of this embodiment, ultrasonic probe disinfecting system 20 of the present invention also incorporates connections or fittings mounted to housing 21 for providing water inlet 41 and waste outlet 42. In the preferred construction, water inlet 41 incorporates water filtration components mounted therein, constructed for assuring that any water delivered to housing 21 is filtered to a high level or standard for use by system 20 in providing the desired disinfection of probe assembly 22.

Finally, system 20 of the present invention also preferably incorporates suitable cover means cooperatively associated with base 21 for overlying and covering base 21 in its entirety, or, if desired, for covering all areas where fumes from the disinfecting solution could escape. In this way, exposure of the fumes of the disinfecting solution to individuals is prevented.

Furthermore, in the preferred construction, an air filtration system is incorporated into housing 21 which incorporates specific air filters constructed to remove and neutralize the disinfectant fumes generated by the solution. In its preferred construction, a blower is also employed to drive the air away from the source of the fumes and delivery of the air through the filter before recirculating the filtered air into the ambient surroundings.

By employing ultrasonic probe disinfecting system 20 of the present invention, any desired transesophageal ultrasonic probe can be quickly and easily mounted in system 20 of the present invention and completely disinfected in a fully automated, computer-controlled, easily employed manner. Typically, the first step employed by any operator in assuring that the desired transesophageal ultrasonic probe is properly disinfected is to remove any bio-burden on the probe assembly by employing an enzyme coated wipe sponge. By thoroughly cleaning all bio-burden from the probe assembly, by merely drawing the elongated shaft and transducer through the enzyme coated wipe sponge, all human protein on the surface of the shaft is removed. This manual wiping process also mechanically removes the bio-burden that may remain on the probe from a previous patient.

Once the outer surface of the flexible shaft of the probe assembly has been manually wiped, the probe assembly is loaded into automated disinfecting system 20 of this invention. As fully detailed above, this loading is quickly and easily achieved by telescopically advancing transducer 25 and flexible shaft 25 into elongated, probe receiving and holding cavity/passageway 28. Once the entire length of flexible shaft 24 of probe assembly 22 has been fully extended into cavity/passageway 28, electronics containing section 23 is mounted to holding and supporting platform 32, where section 23 is securely retained with the electronics thereof secured and positioned for preventing any exposure thereof to any disinfecting solutions and/or rinse water.

In the preferred embodiment, panel 40 will initially display a request for the operator to select whether a leak test should be performed on probe assembly 22. If the leak test is desired, a salt tablet is placed in cavity/passageway 28 prior to loading probe assembly 22 therein and, once the probe assembly has been fully inserted into cavity/passageway 28, the start button of panel 40 is pressed to begin the process.

Figure 9:
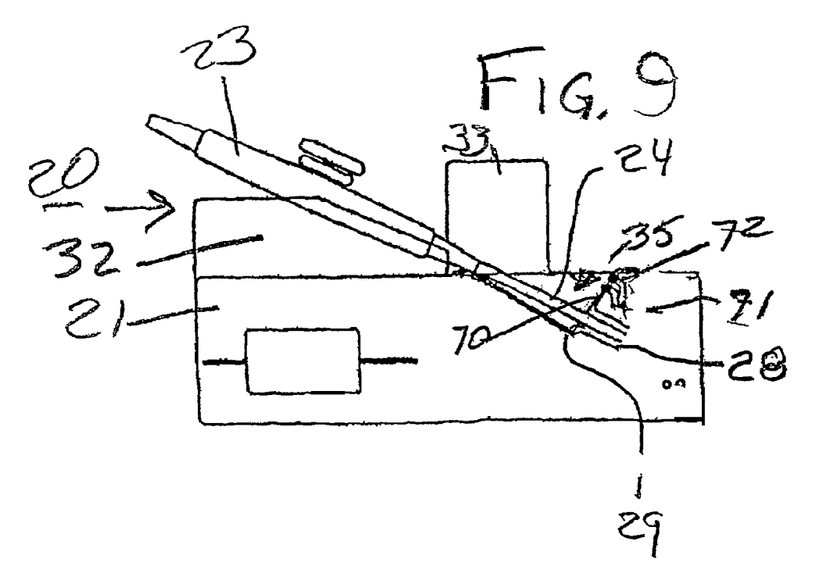
FIG. 9 is a side elevation view of the fully assembled, automated disinfection system of FIG. 1.
Figure 10:
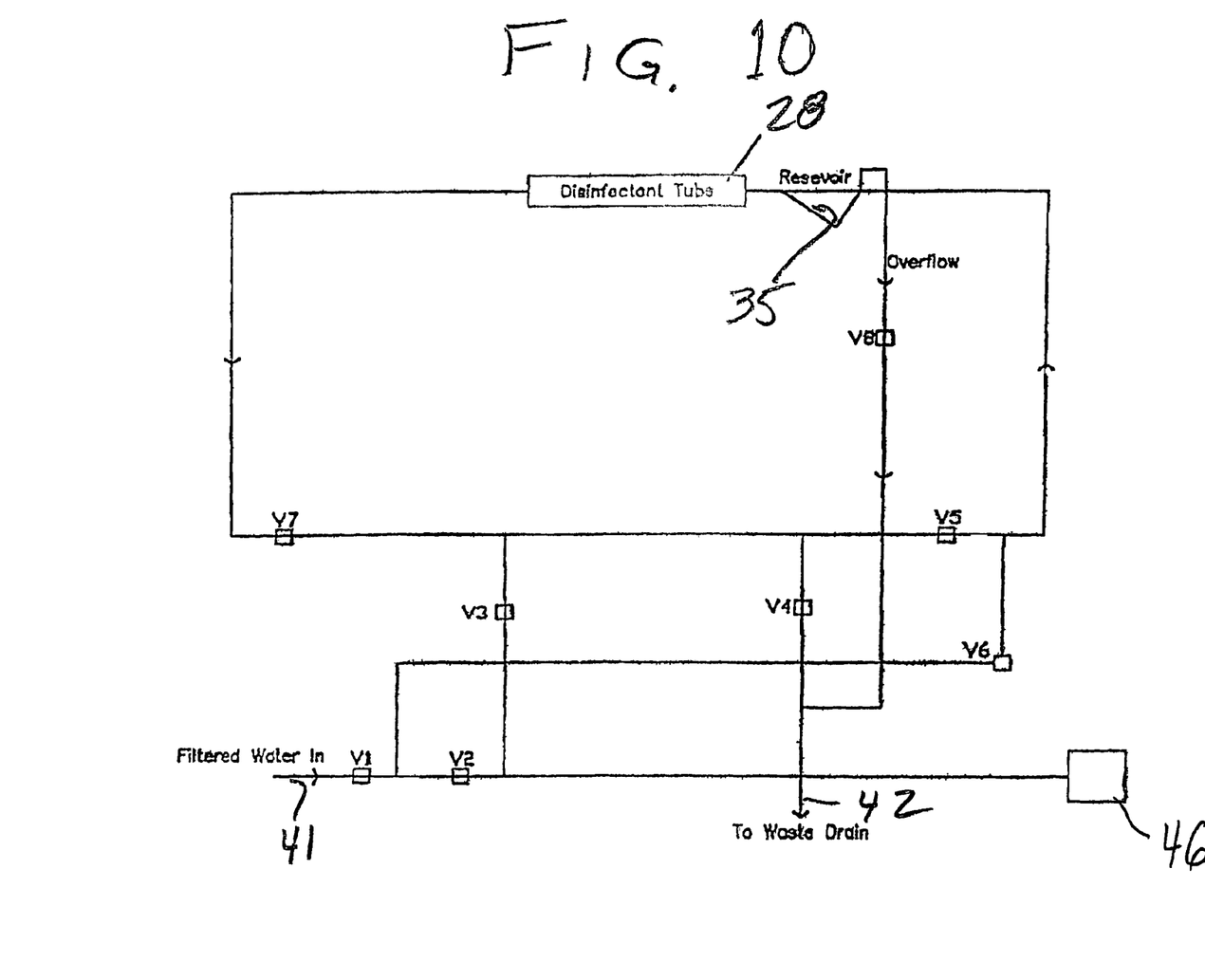
FIG. 10 is a schematic block diagram showing the layout of the various automatically controlled valve member's incorporated into the fully assembled, automated disinfection system of the present invention.

By referring to FIG. 9, along with the following detailed discussion, the automated operation of ultrasonic probe disinfecting system 20 of the present invention can best be understood. In addition, the automated opening and closing of the cooperating valve members associated with system 20 are discussed in conjunction with the depiction of these valve members in FIG. 9.

In this regard, the first step in conducting a leak test is to open valve V1 and V6 which enables filtered water to be delivered to reservoir 35 and cavity/passageway 28. Once cavity/passageway 28 has been filled with water, valves V1 and V6 are closed. Prior to conducting the leak test, system 20 establishes that conductivity does exist through cavity/passageway 28 by passing current between two electrodes. When conductivity has been demonstrated, the leak test is conducted.

Since the water in cavity/passageway 28 contains traces of salt or sodium chloride, the electrical conductivity can be checked between the internal electrodes of the probe and a metal connector which is in contact with the water in cavity/passageway 28 at the distal end thereof. Since the probe is coated in a non-conductive material, any current detected means that leakage has occurred between the electrodes within the probe and the exterior surface of the probe. If such leakage is detected, the user is prompted by panel 40 that leakage has been found and the user may abort the rest of the cycle or may continue.

The next step in the process is to mount the sealed disinfectant bearing container in docking station 33 and activate the system to assure that the container seal is ruptured to enable the disinfectant solution to be withdrawn from the container. At this time, housing 20 should be enclosed by the associated cover to assure that fumes generated by the disinfectant solution are controlled and the operator is not exposed to the fumes.

At this stage, disinfecting system 20 automatically cycles through each of the pre-determined stages which assures that probe assembly 22 is fully disinfected. In the preferred embodiment, the first cycle is a pre-rinse cycle wherein the associated pump is activated and filtered water is allowed to continuously flush through cavity/passageway 28, while being withdrawn and delivered to waste outlet 42. In the preferred operation, this pre-rinse cycle continues for up to about two minutes.

In order to achieve the desired pre-rinsing and flushing of shaft 24 and transducer 25 of probe assembly 22, the pump associated with system 20 is activated and operated during the entire cycle. In addition, valves V1, V4, V6, and V7 are opened and remain open during the entire cycle. As is evident from the diagram of FIG. 9, this arrangement enables the filtered water to flow from water inlet 41 to reservoir 35 and into cavity/passageway 28 for filling cavity/passageway 28, and then flow therefrom to waste outlet 42.

The next cycle is a disinfectant fill and soak cycle wherein flexible shaft 24 and transducer 25 of probe assembly 22 is continuously exposed to the concentrated disinfectant for an extended period of time. In accomplishing this cycle, the first step is to completely evacuate cavity/passageway 28 of all liquid by delivering any such liquid to waste drain 42. When completed, drain 42 is closed along with the open valve members.

The next step is to completely fill cavity/passageway 28 with the disinfectant solution. This is achieved by turning on the pump and opening valves V3 and V5. Once cavity/passageway 28 is completely filled with the disinfectant solution, bringing the solution into direct contact with flexible shaft 24 and transducer 25, the pump is turned off and the valves are closed. The probe assembly is then allowed to soak in the disinfectant solution for an extended period of time. In the preferred embodiment, a soak time of about one minute is employed.

Once the soak time has been completed, the disinfectant is cycled continuously through cavity/passageway 28 from the distal end thereof to the reservoir and portal end. In this regard, any desired disinfectant recycling time can be employed. However, a recycled time of about nine minutes has been found to be optimal.

In order to achieve the disinfectant recycling, the pump is turned on and valves V5 and V7 are opened and maintained open for the entire period of time. Once the recycled time period has elapsed, the pump is turned off and the valves are closed.

The next step in disinfecting probe assembly 22 is to drain the disinfectant from the system. In the preferred operation, the disinfectant is drained to waste drain 42 while being intermixed with water in order to dilute the concentration of the disinfectant. In achieving this result, the pump is turned on and valves V1, V4, V6 and V7 are opened and remain open for the entire drain cycle. Generally, it has been found that this cycle should continue for about two minutes, in order to assure complete removal and dilution of the disinfectant solution.

In the next step, the disinfectant bearing container and delivery lines are automatically disinfected and flushed. In achieving this result, valves V1 in V2 are opened while valve V6 is closed for a period of time just long enough to fill the disinfectant bearing container. Once the container is filled with water, valves V1 and V2 are closed and the pump is turned on. Then, with valves V3 and V4 open, the contents of the solution bearing container are directed to waste drain 42.

Preferably, this cycle is repeated at least two times, until the container has been fully flushed of all significant traces of the disinfectant.

In the final step, a final rinse of cavity/passageway 28 is provided. Preferably, the final rinse is conducted for approximately four minutes in order to remove all traces of the disinfectant therefrom. Once the final rinse cycle has been concluded, water inlet 41 is closed and all of the water in cavity/passage-way 28 is delivered to drain 42. In achieving the final rinse cycle, the pump is turned on and valves V1, V4, V6 and V7 are opened.

Although fully detailed above, Table II is provided for assuring a full and complete disclosure of the pump and valve sequencing. As is evident from a review of Table II, the pump and valve control operation and status for each of the steps is provided.

TABLE II

| Cycle | Pump | V1 | V2 | V3 | V4 | V5 | V6 | V7 |
|---|---|---|---|---|---|---|---|---|
| Leak Test | Off | On to fill | Off | Off | Off | Off | On to fill | Off |
| Pre-Rinse | On | On CT | Off | Off | On CT | Off | On CT | On CT |
| Glutaraldehyde Soak | On to fill | Off | Off | On to fill | Off | On to fill | Off | Off |
| Glutaraldehyde Drain | On CT | On CT | Off | Off | On CT | Off | On CT | On CT |
| Container Rinse In | Off | On CT | On CT | Off | Off | Off | Off | Off |
| Container Rinse Out | On CT | Off | Off | On CT | On CT | Off | Off | Off |
| Final Rinse | On CT | On CT | Off | Off | On CT | Off | On CT | On CT |

Once all of the cycles have been completed, panel 40 displays an appropriate message, such as cycle end, and the ultrasonic probe assembly 22 is completely disinfected, ready to be removed and re-used. Furthermore, in the preferred embodiment, a thermal printer is interconnected with system 20 in order to provide a complete summary of the machine operation and a validation of the procedure and its completion.

It will thus be seen that the object set forth above, among those made apparent from the preceding description, are efficiently attained and, since certain changes may be made in the above constructions without departing from the scope of the invention, it is intended that all matter contained in the above description or shown in the accompanying drawings shall be interpreted as illustrative and not a limiting sense.

It is also to be understood that the following claims are intended to cover all of the generic and specific features of the invention herein described, and all statements of the scope of the invention which, as a matter of language, might be said to fall therebetween.

The invention claimed is:

1. A fully automated disinfection system for use with transesophageal ultrasonic probe assemblies incorporating an electronics containing portion and an elongated flexible shaft extending therefrom and terminating with a transducer, said disinfection system comprising:
   A. a housing;
   B. an elongated passageway supportingly mounted in the housing and constructed for receiving and retaining the flexible shaft and transducer of the ultrasonic probe assembly in their entirety, said passageway comprising a continuous, smooth, elongated pathway having a proximal end and a distal end, with the distal end representing the lowest point of said elongated passageway, wherein said proximal end comprises a first substantially straight section, said distal end comprises a second substantially straight section, and an intermediate arcuately curved section is formed between and interconnects the first substantially straight section and the second substantially straight section;
   C. a holding member positioned in association with the elongated passage-way for receiving and retaining the electronics containing portion of the probe assembly in a position free from exposure to any disinfection solution;
   D. a disinfection solution dispensing section positioned in association with the elongated passageway and constructed for receiving a quantity of disinfection solution and dispensing the disinfection solution to the passageway for contact with the flexible shaft of the ultrasonic probe assembly;
   E. circulation means constructed for circulating the disinfection solution through the passageway to provide complete disinfection of the outer surface of the flexible shaft of the ultrasonic probe assembly; and
   F. control means for providing automatic activation and de-activation of the circulation means to achieve the required operational steps to assure complete disinfection of the flexible shaft of the ultrasonic probe assembly;

whereby a single system is achieved for providing complete, automated disinfection of any desired ultrasonic probe assembly without requiring any operator intervention.

2. The fully automated disinfection system defined in claim 1, wherein said intermediate arcuately curved section is further defined as comprising an arcuately curved section which does not exceed 90°.

3. The fully automated disinfection system defined in claim 1, wherein the disinfection solution dispensing section incorporates a quantity of a disinfection solution and said disinfection solution comprises between about 2.5% and 3.0% by weight based upon the weight of the entire composition of glutaraldehyde.

4. The fully automated disinfection system defined in claim 3, wherein said disinfection solution is further defined as being contained in a single use container.

5. The fully automated disinfection system defined in claim 3, wherein said system further comprises a closed loop conduit path extending between the proximal end of said passageway, the solution dispensing section, and the distal end of said passageway.

6. The fully automated disinfection system defined in claim 5, wherein said system further comprises a heater mounted in said closed conduit path and constructed for heating the disinfection solution during its passage through said closed loop path.

7. The fully automated disinfection system defined in claim 6, wherein said heater is further defined as being constructed for maintaining the temperature of the disinfection solution between about 35° C. and 45° C. during its circulation through said closed loop path.

8. The fully automated disinfection system defined in claim 6, wherein the circulation means is further defined as comprising a pump and a plurality of valves constructed for being responsive to control signals for opening and closing said valves.

9. The fully automated disinfection system defined in claim 4, wherein said disinfection solution dispensing section is further defined as comprising container receiving means for enabling the placement and securement of the disinfectant container in direct association therewith, and seal rupturing means for automatically breaking any seal mechanism associated with the disinfectant container.

10. The fully automated disinfection system defined in claim 3, wherein said system further comprises an air circulation fan and filter mounted within said housing for controlling the odors of all materials contained within said housing and passing said odor laden materials through said filter prior to discharging the filtered air from the interior of said housing.

11. The fully automated disinfection system defined in claim 10, wherein said control means is further defined as comprising a computer-based electronics assembly constructed for controlling all components contained within said system and providing control signals for opening and closing the plurality of valves in a predefined sequence for providing passage of the disinfection solution through the passageway in a manner which assures disinfection of the flexible shaft and transducer of the ultrasonic probe.

12. The fully automated disinfection system defined in claim 11, wherein said system further comprises a water inlet portal for receiving water and delivering the water to the circulation means for enabling the controlled passage of the water through the passageway for rinsing the flexible tube and transducer of the ultrasonic probe assembly after application of the disinfection solution.

13. The fully automated disinfection system defined in claim 12, wherein the computer-based electronics assembly of the control means is further constructed for providing repeated rinse cycles for removing all disinfection solution from the flexible shaft and transducer of the ultrasonic probe assembly, the empty container and the closed loop conduit path.

14. The fully automated disinfection system defined in claim 1, wherein said system further comprises an input panel directly associated with the control means for enabling relevant data to be provided to the control means by the operator.

15. The fully automated disinfection system defined in claim 14, wherein said input panel is employed for providing one or more control data selected from the group consisting of identifying indicia of the ultrasonic probe assembly, identifying indicia of the disinfectant solution container, process parameters, and special instructions.

16. The fully automated disinfection system defined in claim 15, wherein said system is further defined as comprising a printer assembly cooperatively associated therewith for providing relevant information data to the operator after the completion of the disinfection cycle.

* * * * *